United States Patent
Schumacher

(10) Patent No.: US 6,583,406 B2
(45) Date of Patent: Jun. 24, 2003

(54) DEVICE FOR DETECTING CHARACTERISTICS OF A MOVING PAPER WEB, SAID DEVICE COMPRISING A POLYCHROMATOR AND AN IR DETECTOR MATRIX

(75) Inventor: Ursula Schumacher, Jülich (DE)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 10/166,998

(22) Filed: Jun. 11, 2002

(65) Prior Publication Data

US 2002/0179831 A1 Dec. 5, 2002

Related U.S. Application Data

(63) Continuation of application No. PCT/DE00/04086, filed on Nov. 18, 2000.

(30) Foreign Application Priority Data

Dec. 11, 1999 (DE) .......................... 199 59 762

(51) Int. Cl.[7] .............................................. G01N 21/86
(52) U.S. Cl. ................................. 250/252.1; 250/339.11
(58) Field of Search .......................... 250/252.1, 339.11, 250/338.1, 341.8, 559.02, 226, 559.04; 356/407, 408, 425, 73

(56) References Cited

U.S. PATENT DOCUMENTS

| 4,692,026 A | * | 9/1987 | Gawrisch et al. ............ 356/345 |
| 5,365,084 A | * | 11/1994 | Cochran et al. ............. 250/571 |
| 5,778,041 A | * | 7/1998 | Chase et al. ................... 378/53 |
| 6,272,440 B1 | * | 8/2001 | Shakespeare et al. ......... 702/85 |

* cited by examiner

*Primary Examiner*—Constantine Hannaher
*Assistant Examiner*—Otilia Gabor
(74) *Attorney, Agent, or Firm*—Alston & Bird LLP

(57) ABSTRACT

An infrared detector device for a device for detecting properties of a moving web of paper, more specifically for a device for controlling production in the paper making process, the detector device being provided, on the one side, with a polychromator that receives, on its receiving side, light coming from the web of paper and, on the other side, with an infrared detector with a matrix of infrared sensitive photoconductors, an evaluation electronic unit with one memory assigned to a respective one of the photoconductors of the matrix being connected downstream thereof. An additional source of light that can be controllably switched on and off between a first light intensity and a second light intensity which is greater than the first one uniformly illuminates the infrared detector for deriving correction values for correcting the signals from each of the photoconductors during a measurement.

10 Claims, 1 Drawing Sheet

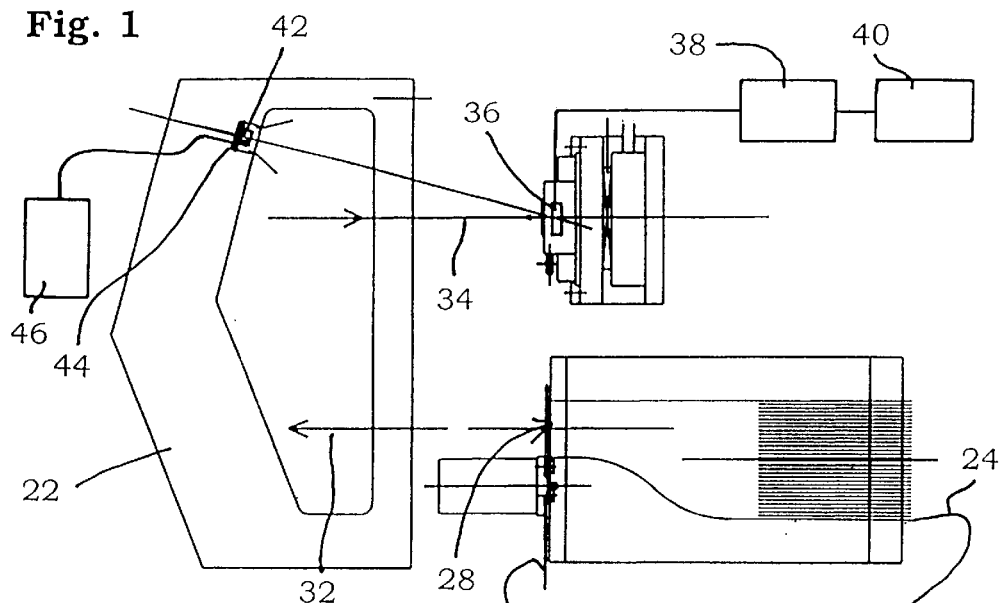
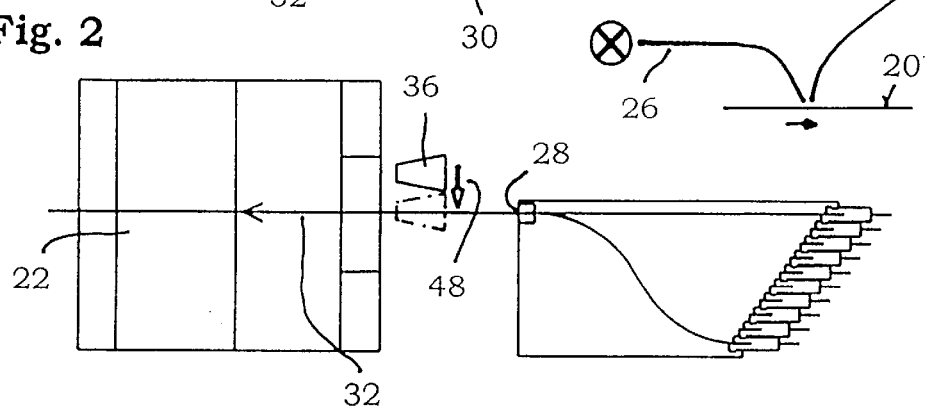
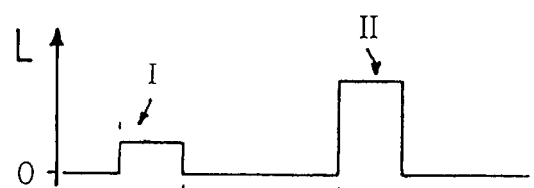
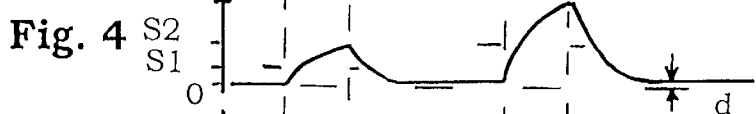
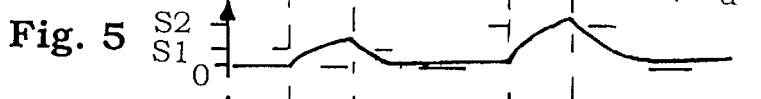
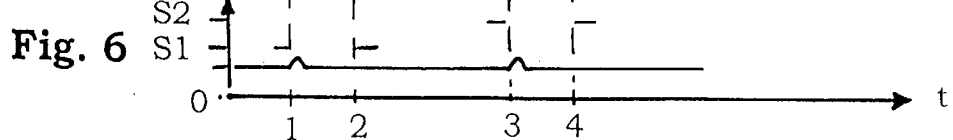

DEVICE FOR DETECTING CHARACTERISTICS OF A MOVING PAPER WEB, SAID DEVICE COMPRISING A POLYCHROMATOR AND AN IR DETECTOR MATRIX

CROSS-REFERENCE TO RELATED APPLICATIONS

This application is a continuation of International Patent Application PCT/DE00/04086 filed Nov. 18, 2000, which is incorporated herein by reference.

FIELD OF THE INVENTION

The invention relates to an infrared detector device for detecting properties of a moving web of paper, more specifically for use in controlling production in a paper making process, the detector device being provided, on one side thereof, with a polychromator that receives light coming from the web of paper and, on the other side, with an infrared detector having a matrix of infrared sensitive photoconductors, and an evaluation electronic unit with a separate memory assigned to each of the photoconductors of the matrix being connected downstream thereof. The invention also relates to a method for operating such an infrared detector device.

BACKGROUND OF THE INVENTION

A device of this type is described in PCT/DE 99/02530. Such matrix detectors are mainly utilized for image digitization; for example, they are known to have been used for night viewing apparatuses. They consist of a matrix of individual pixels, each pixel being a photoconductor. By photoconductor is meant a photosensitive electrical element that generates an electric current or voltage change when illuminated. More specifically, possible photoconductors are infrared sensitive semi-conductors, e.g., PbS, CCD, and CMOS arrays.

The problem with infrared detectors of the type mentioned above is that the individual pixels or photoconductors have differing properties. In particular they tend to differ in offset and sensitivity.

With the infrared detector device of the type mentioned above, it is important for the result of the measurement that the behavior of each and every one of the pixels of the detector matrix is the same as that of all the others. The web of paper is sensed by regions for detecting defects or deviations thereof. Sensing is carried out in what are termed measuring dots. Usually, a great number of such measuring dots is arranged over the width of the conveyed web of paper. At least one pixel, preferably a complete line or row of pixels, is assigned to a respective one of the measuring dots. Their properties are crucial to the result of the test for determining whether a web of paper meets the required standards or not.

SUMMARY OF THE INVENTION

In view of the above, it is the object of the invention to improve an infrared detector device of the type mentioned, and to provide a method for operating such a device, aimed at equalizing the behavior of the pixels in the result of the measurement and at conferring controllable properties onto the pixels. More specifically, the invention aims at excluding pixels below standard, which cannot be used in practice for any reason, more specifically because they are too insensitive, so that these pixels do not influence the result of the measurement.

The solution to this object, with regard to the device, is to provide it with an additional source of light that can be controllably switched on and off between a first light intensity and a second light intensity which is greater than the first one. The additional source uniformly illuminates the infrared detector and is arranged so that it does not hinder (at least not when in its switched-off condition) the beam path of the light passing through the polychromator and illuminating the infrared detector.

In accordance with the invention, a method for operating an infrared detector device as specified in the previous paragraph is provided, in which the additional source of light is operated at the first light intensity and the thereby obtained electrical signals of every photoconductor are acquired, in which the additional source of light is operated at the second light intensity and the thereby obtained electrical signals of every photoconductor are again acquired, and in which, by comparison with a reference pixel, first and second correction values for each of the photoconductors are obtained based on the electrical signals. The two correction values for every photoconductor are saved and taken into consideration in later measurement.

Thus, in accordance with the invention, the detector matrix is homogeneously illuminated by means of an additional light source. This occurs out of a measuring phase, in what is termed a test phase. During the test phase, no other light, no entering light in particular, is allowed to be incident upon the detector matrix. If necessary, such a light is shaded. If no suited means, such as a chopper for example, is provided, it is advantageous to provide for an appropriate device such as a shutter or a closure for example.

In accordance with the invention, each pixel has been assigned a memory of its own. Within a greater memory, a certain address is assigned to only that specific pixel. The correction values obtained in the test phase are saved in the memory and are used to correct measured values of the signals of the individual pixels obtained later on in the measuring phase, the corrected measured values then being outputted.

With regard to the method, the test phase is carried out in the light and in the dark. In the light, two different light intensities are used, i.e., a first light intensity and a second light intensity, which is greater than the first one. Preferably, the two light intensities are within the range of the light intensity generated by the entering light onto the respective pixels. Accordingly, the first light intensity preferably is within the lower intensity range of the entering light and the second light intensity preferably within the upper intensity range of the entering light to be measured. The additional source of light is operated accordingly.

The correction of every single pixel is made according to a linear equation, i.e., according to a line equation with a gradient as a first correction value and with an offset or Y-axis intercept as a second correction value. Correction is made for the electrical signals of every single pixel obtained both in the dark and in the light.

Preferably, an infrared light emitting diode (IR-LED) is used as the additional source of light. It is preferably associated with a temperature control device that keeps the temperature of the diode constant. The temperature is preferably below room temperature, so that the LED is being cooled. In a preferred embodiment, this is achieved by means of a Peltier element which is assigned a temperature sensor and a control circuit.

In a preferred embodiment, the additional source of light is located inside a polychromator. It is arranged in such a manner that it directly illuminates the detector matrix through the exit window. It is located at a distance of some centimeters from the detector matrix and in the beam path behind the element in the polychromator that splits the light, i.e., a grating or a prism.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 is a diagrammatic top view of an infrared detector device,

FIG. 2 is a side view of a device according to FIG. 1, but now with a retractable and collapsible additional light source, FIG. 3 is a diagram of the curve of the light intensity L of the additional light source outlined over time t, FIG. 4 shows the curve of the voltage applied to a first pixel over time t and within the same period of time during illumination by the additional light source according to FIG. 3, FIG. 5 shows a curve according to FIG. 4, but for another pixel and FIG. 6 shows a curve according to FIG. 3, but for a defective pixel.

DETAILED DESCRIPTION OF PREFERRED EMBODIMENTS

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

As more specifically shown in FIG. 1, the infrared detector device of a device for detecting properties of a moving web of paper 20 has a polychromator 22 receiving, on the receiving side, light transmitted from the web of paper 20 by way of a plurality of optical fibers 24. On the input side, the individual optical fibers 24 are directed onto measuring dots on the web of paper 20. These measuring dots are illuminated by an illumination array 26 provided with an infrared light source and an optical fiber. The web of paper 20 is conveyed in the direction indicated by the arrow. In FIG. 1, only one of all the many optical fibers 24 is drawn; it will be understood that the others are lying parallel to the depicted fiber and are bundled into a slit 28 forming the entrance slit of the polychromator 22. In the immediate proximity to this slit 28, there is also located a chopper 30 with a chopper disc of well-known construction. As a result thereof, the light traveling along the arrow 32 and representing the light entering the polychromator 22 is periodically interrupted.

After the light has passed through the polychromator 22, the light of every single optical fiber, which is now split in a spectrum transversely to the orientation of the slit 28, impinges on an infrared detector 36. The latter is connected to an evaluation circuit 38 and to a memory 40.

The infrared detector 36 has a matrix of individual infrared sensitive pixels that are arranged in a checkerboard pattern. Such infrared detectors are well known in the art, as disclosed in PCT/DE 99/02530 for example.

To permit testing and adjusting of the individual pixels of the infrared detector 36 during a test phase as well as consideration of the correction values obtained in later measurements, additional provisions are made as explained below.

In the polychromator, outside of the effective beam path as it is substantially shown by the arrows 32, 34, there is arranged an additional source of light 42 in the form of an infrared light emitting diode. Through an exit window of the polychromator 22, the source 42 emits a ray of light oriented diagonally toward the infrared detector 36 which it illuminates completely and uniformly. The selected spacing permits to achieve the complete and uniform illumination. The source of light is spaced from the infrared detector preferably by a distance of about 5–40 cm.

The temperature of the infrared light emitting diode preferably is controlled to be substantially constant; preferably, the diode is cooled by a cooling device such as a Peltier element 44 that is supplied with current under the control of a control circuit 46. The Peltier element 44 is assigned a temperature sensor which is also electrically connected to the control circuit 46.

The control circuit is also electrically connected to the light source 42 which it supplies with current. Controlled by a general control of the overall device that is not illustrated herein, a PC for example, the control circuit 46 supplies the light source 42 with an electric voltage whose curve substantially corresponds to the curve of the light current L generated, as a result thereof, by said light source, said curve being shown in FIG. 3. According to this curve, the light source 42 has, on the one side, a first condition I with a first light intensity which is represented by a smaller rectangular signal in FIG. 3 and then a second condition II with a higher light intensity, which is represented by a higher rectangle in FIG. 3. As shown in FIG. 3, the additional light source 42 does not emit any light except in these two conditions, the light current amounting then to 0. As a result thereof, the light source does not disturb normal measurement. It is sufficient to switch the light source off. Special darkening provisions, such as a shutter for example, are not necessary.

FIG. 4 shows the response of an efficient pixel to the illumination of FIG. 3. As can be ascertained from FIG. 4, the electrical signal rises, the gradient becoming increasingly flatter, and reaches the maximum value at switch-off time. Then, the signal returns toward the zero line without reaching it altogether, though. The deviation from zero is called drift d. The same is repeated at the second intensity of the light source 42. Again, the signal rises sharply and reaches its maximum at switch-off time from where it decreases again.

FIG. 5 shows a corresponding behavior of a pixel which is not so efficient but still functioning. Here, the signal describes the same curves, but for the amplitudes which are not too high.

FIG. 6 finally shows the result of a defective pixel whose signal is not to be evaluated, since the still obtained, small signal may cause interferences. Such a pixel must be disabled so that its signal is not allowed to be considered for evaluation. The same applies to a pixel that would not respond at all.

To permit exclusion of defective pixels like the one in FIG. 6, threshold values S1 for the condition of the first light intensity and S2 for the condition of the second light intensity are set. They are shown in FIGS. 4 through 6 for all the three pixels shown. As can be seen, both signals of the pixels according to the FIGS. 4 and 5 exceed the respective one of the values S1 and S2. This however is not the case with the pixel of FIG. 6 which remains below the two threshold values in the two conditions I and II. Even though a signal remains below the corresponding threshold value in only one condition, the signal of that pixel is excluded from measurement.

Correction is only made for the pixels considered as effective. For each good pixel, an offset correction factor and a gradient correction factor are computed. For this purpose, a straight line is drawn for each pixel in a system of coordinates, in other words, a linear equation is set up.

More particularly, a reference pixel is selected, which has the desired properties. Its amplitudes in the two cases of illumination I and II are indicated with X1 and X2 on the X-axis. The individual signals of the respective pixels, which are readable in the FIGS. 4 and 5, are indicated as Y1 and Y2. The pair of values X1/Y1 forms a first point, the pair of values X2/Y2, a second point. These two points define a straight line. Now, the inverse function is computed and the gradient correction factor and the offset correction factor are read. In a subsequent measurement, the signal of every good pixel is corrected by multiplying the respective one of the measured electrical signals with the gradient correction factor and by subsequently adding the offset correction factor. The result is the measured value which is taken into consideration in processing the signal.

FIG. 2 is a side view showing how ten individual optical fibers 24 are bundled into an entrance slit 28 oriented transversely to the plane of the paper. The additional light source in the form of an IR-LED is located in a housing between polychromator 22 and infrared detector 36 above the optical axis (arrow 34). The housing can be pivoted downward in the direction indicated by the arrow 48 and adopts then the position shown in dash-dot line in which it is situated within the optical beam path.

All of the embodiments also apply to an infrared detector 36 with a linear array of pixels.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An infrared detector device for detecting properties of a moving web of paper, the detector device comprising:

a polychromator that receives light coming from the web of paper and an infrared detector with a matrix of infrared sensitive photoconductors arranged to receive light from the polychromator;

an additional source of light arranged to uniformly illuminate the infrared detector, the source being controllably switchable on and off between a first light intensity and a second light intensity greater than the first light intensity, the source at least in its switched-off condition allowing unhindered passage of light along an effective beam path through the polychromator to the infrared detector; and an evaluation electronic unit connected with the matrix of the infrared detector, the evaluation electronic unit having a memory assigned to the photoconductors of the matrix, wherein the evaluation electronic unit is operable to:
  a) acquire electrical signals from every single photoconductor obtained at the first and at the second light intensity,
  b) use the thereby obtained electrical signals of a selected photoconductor as reference values,
  c) obtain, for every single photoconductor, based on the electrical signals thereof and the reference values, a first correction value and a second correction value, and
  d) store both correction values for every single photoconductor in the memory.

2. The infrared detector device according to claim 1, wherein the additional light source is arranged within said polychromator outside of the effective beam path of the light passing through to the infrared detector, said polychromator being provided with an exit window for exiting light and wherein the light of the additional light source exits the polychromator through the exit window thereof.

3. The infrared detector device according to claim 1, wherein the additional light source is movable into and out of the effective beam path.

4. The infrared detector device according to claim 1, wherein the additional light source is an infrared light emitting diode.

5. The infrared detector device according to claim 4, wherein the light emitting diode is connected to a facility for stabilizing the temperature of the light emitting diode.

6. The infrared detector device according to claim 5, wherein the facility for stabilizing the temperature comprises a Peltier element.

7. The infrared detector device according to claim 4, wherein the light emitting diode is connected to a device for cooling the light emitting diode.

8. A method of operating an infrared detector device according to claim 1, comprising the steps of:

operating the additional light source at the first light intensity and acquiring the thereby obtained electrical signals from every photoconductor;

operating the additional source of light at the second light intensity and again acquiring the thereby obtained electrical signals from every photoconductor;

designating the obtained electrical signals of a selected photoconductor as reference values;

determining a first correction value and a second correction value for every single photoconductor based on the electrical signals thereof and the reference values;

saving the two correction values for each photoconductor; and taking the correction values for each photoconductor into consideration during a measurement operation.

9. The method of operating an infrared detector device according to claim 8, wherein light entering the polychromator is prevented from illuminating the infrared detector during evaluation of the correction values.

10. The method of operating an infrared detector device according to claim 8, wherein respective threshold values (S1, S2) are set for the electrical signals at the first and second light intensities and wherein only those photoconductors are taken into consideration whose signals are, at both light intensities, above the respective threshold value (S1, S2).

* * * * *

UNITED STATES PATENT AND TRADEMARK OFFICE
CERTIFICATE OF CORRECTION

PATENT NO. : 6,583,406 B2 Page 1 of 1
DATED : June 24, 2003
INVENTOR(S) : Schumacher It is certified that error appears in the above-identified patent and that said Letters Patent is hereby corrected as shown below:

Title page,
Item [56], References Cited, insert the following:
-- FOREIGN PATENT DOCUMENTS
GB     2 314 227 A    12/1997
WO    WO 00/26648   5/2000 --.

Signed and Sealed this

Fourteenth Day of October, 2003

JAMES E. ROGAN
*Director of the United States Patent and Trademark Office*